(12) United States Patent
Frigoli et al.

(10) Patent No.: US 7,273,937 B2
(45) Date of Patent: Sep. 25, 2007

(54) PROCESS FOR THE PREPARATION OF TAZAROTENE

(75) Inventors: Samuele Frigoli, Legnano (IT); Claudio Fuganti, Milan (IT); Stefano Serra, Usmate-Velate (IT); Francesco Pizzocaro, Garbagnate (IT); Angelo Bedeschi, Garbagnate (IT); Paolo Tubertini, Garbagnate (IT)

(73) Assignee: Solmag S.p.A., Mulazzano (IT)

( * ) Notice: Subject to any disclaimer, the term of this patent is extended or adjusted under 35 U.S.C. 154(b) by 0 days.

(21) Appl. No.: 11/368,486

(22) Filed: Mar. 7, 2006

(65) Prior Publication Data

US 2006/0205950 A1    Sep. 14, 2006

(30) Foreign Application Priority Data

Mar. 8, 2005   (IT)   .......................... MI2005A0357

(51) Int. Cl.
*C07D 409/06*    (2006.01)

(52) U.S. Cl. .................................................. 546/280.1
(58) Field of Classification Search .............. 546/280.1
See application file for complete search history.

(56) References Cited

OTHER PUBLICATIONS

Still et al., "Thiophosphoryl bromide etc.," CA 92:41493 (1979).*
Nagasawa et al., "Organosulfur chemistry, etc.," CA 108: 75185 (!987).*
Frigoli et al., "A Practical and, etc.," Organic Process Research & Development 2005, 9, 646-650.*

* cited by examiner

Primary Examiner—Patricia L. Morris
(74) Attorney, Agent, or Firm—Rothwell Figg Ernst & Manbeck, P.C.

(57) ABSTRACT

Tazarotene is prepared by deoxygenation of the corresponding S-oxide, in turn obtained according to two alternative synthetic pathways.

2 Claims, No Drawings

PROCESS FOR THE PREPARATION OF TAZAROTENE

FIELD OF THE INVENTION

The present invention relates to a novel, improved process for the preparation of ethyl 6-[2-(4,4-dimethylthiochroman-6-yl)ethynyl]nicotinate, Tazarotene, of formula (1), a compound structurally related to retinoic compounds having similar therapeutical applications in dermatological conditions. The usual synthesis of Tazarotene (EP 0 284 261 A1; 28.09.1988; EP 0 284 288 A1; U.S. Pat. No. 5,023,341; U.S. Pat. No. 5,089,509; U.S. Pat. No. 5,659,042; U.S. Pat. No. 5,717,094) involves as key intermediates 4,4-dimethyl-6-ethynylthiochromane (2) and ethyl 6-chloronicotinate (3) which contain all the carbon atoms present in the final molecule, as well as the functionalities required to form the carbon-carbon bond in it (Scheme A).

with lithium diisopropylamide, diethyl chlorophosphate and further lithium diisopropylamide. The low temperatures required involve the use of dedicated reactors, and the use of lithium diisopropylamide, a highly flammable, difficult-to-handle reagent, makes the synthesis of (2) troublesome.

It has now been found that Tazarotene (1) can be prepared more conveniently compared with the prior art processes, by deoxygenation of the corresponding S-oxide (4), obtained from 4,4-dimethyl-6-bromothiochromane-S-oxide (5) according to two different procedures.

According to the invention, starting compounds are easily available and consist of 4-bromothiophenol, 3,3-dimethylallyl bromide, 2-methyl-3-butyn-2-ol and ethyl 6-chloronicotinate; the necessary reactives are inexpensive and the catalysts can be recovered, the reaction conditions are mild and do not require any specific apparatuses, so that the process is advantageous in terms of costs, compared with those described above.

Scheme A

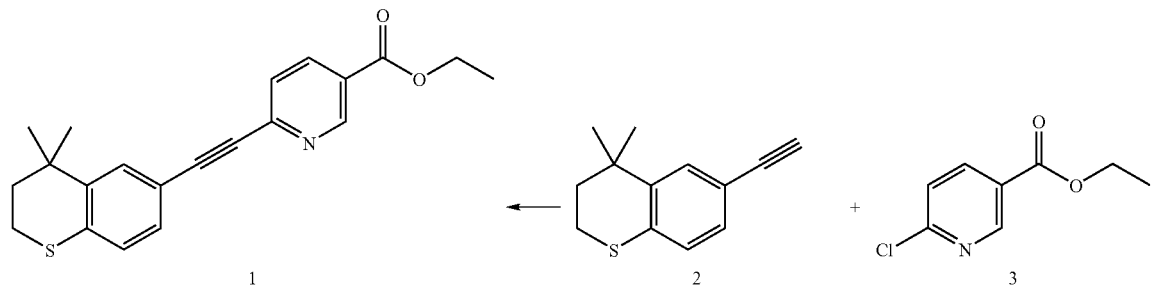

The process of the present invention is based on the deoxygenation of S-oxide (4), obtainable according to different procedures starting from 4,4-dimethyl-6-bromothiochromane-S-oxide (5).

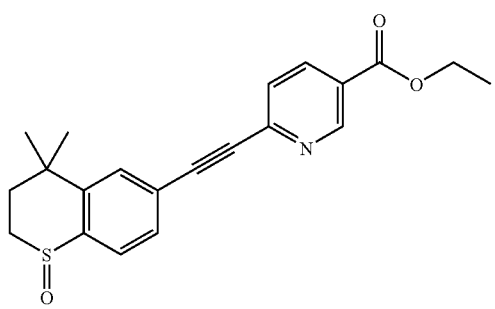

4

DISCLOSURE OF THE INVENTION

The disadvantages involved in the synthesis of 4,4-dimethyl-6-ethynyl-thiochromane (2) as an intermediate (scheme A) make highly desirable to develop novel processes for the preparation of compound (1) starting from different intermediates. The preparation of compound (2) starts with Friedel—Crafts acylation (acetyl chloride/SnCl$_4$ or AlCl$_3$) of 4,4-dimethylthiochromane to give 4,4-dimethyl-6-acetylthiochromane, which is then dehydrated to (2) according to a low-temperature, multi-step procedure carried out in the same reactor and consisting in the treatment In the attempt to prepare 4,4-dimethyl-6-ethynylthiochromane (2) more conveniently than in the prior art methods, 4,4-dimethyl-6-bromothiochromane and 2-methyl-3-butyn-2-ol (6) were reacted under conditions conventionally considered suitable (Negishi, AND.; Anastasia, L. *Chem. Rev.* 2003, 103, 1979-2017; Sonogashira, K.; Tohda, Y.; Hagihara N. *Tetrahedron Lett.* 1975, 50, 4467-4470) to replace the bromine atom on the aromatic ring with the acetylene moiety, but the formation of the desired product was unsuccessful. On the other hand, under the same conditions, 4,4-dimethyl-6-bromothiochromane S-oxide (5) unexpectedly affords the adduct (7) in high yields. The latter is easily converted to 4,4-dimethyl-6-ethynylthiochromane-S-oxide (8) under basic conditions (Scheme B). Compound (8) quantitatively affords intermediate (2) of Scheme A by deoxygenation, for example with PCl$_3$ in N,N-dimethylformamide (DMF) at temperatures ranging from −25° C. to −15° C.

Scheme B

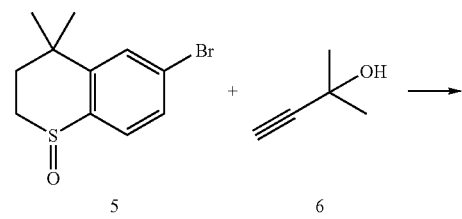

Tazarotene (1), based on the condensation of ethyl 6-ethynylpiridin-3-carboxylate (10) with 6-bromothiochromane S-oxide (5). The reaction of butynol (6) with the ester (3) under the conditions reported above for this kind of coupling yields adduct (9), that is converted to the acetylene derivative (10) under basic controlled conditions (Scheme D):

Scheme D

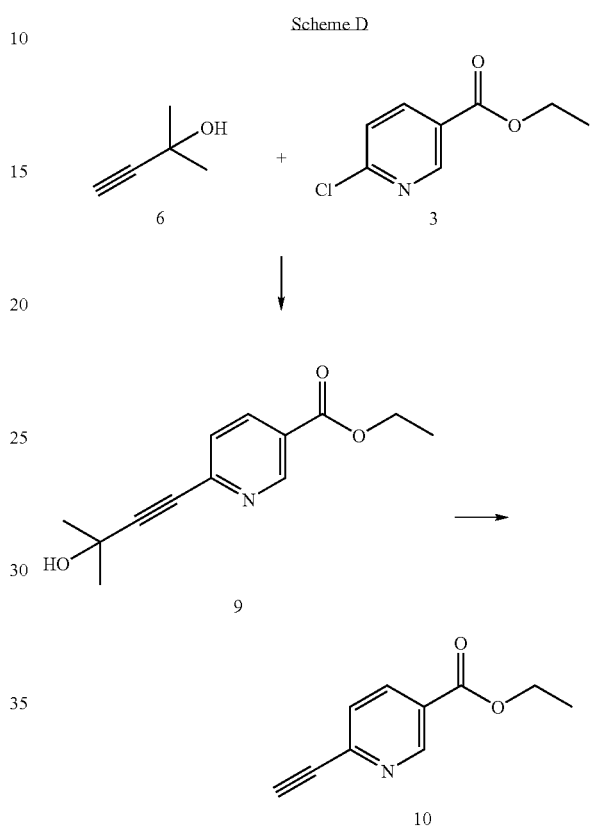

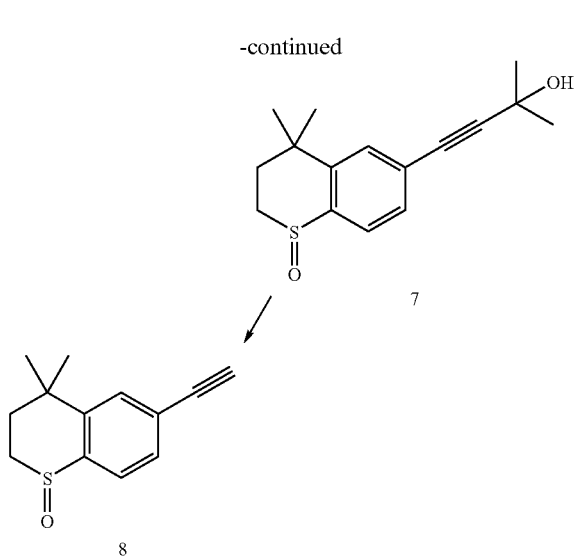

The process for the preparation of (2) from (8) according to the invention is novel and is per se an improvement over the procedure of the prior art for the preparation of Tazarotene (1), in that it avoids the problems involved in the synthesis of (2) as described above. However, it has been found that, for preparing Tazarotene (1), the oxygen linked to the sulfur atom of (8) should be removed in the subsequent steps, as compound (8), when reacted under suitable conditions with ethyl 6-chloronicotinate (3), affords highly crystalline, S-oxide (4), which is easily purified, in high yields (Scheme C). An unexpected, advantageous feature of the processes of the invention is indeed the high crystallinity imparted by the S-oxide moiety not only to compound (4), but to the various intermediates as well. Finally, Tazarotene (1) is obtained from (4) by deoxygenation, for example according to the procedure as described for the conversion of (8) to (2).

Scheme C

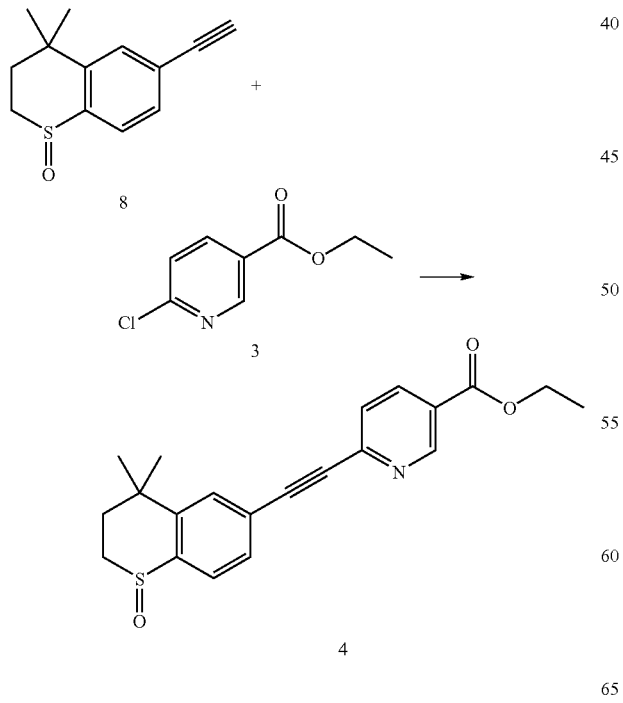

The easiness of purification of S-oxide (4) induced the Applicant to investigate for further synthetic routes for Finally, condensation of (5) with (10) in the presence of bis(triphenylphosphine) palladium(II) dichloride, copper(I) iodide and triethylamine in N,N-dimethylformamide at about 50° C. affords (4), which yields Tazarotene (1) under the conditions already described (Scheme E):

Scheme E

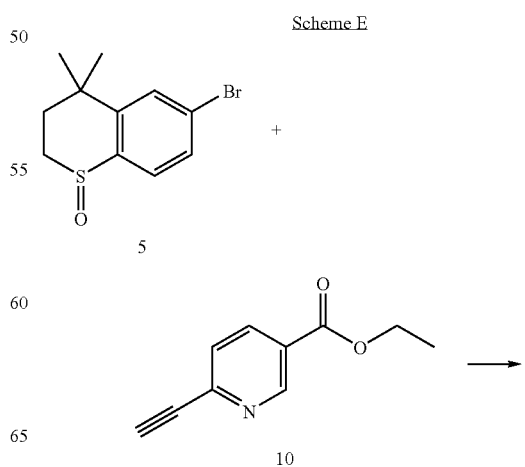

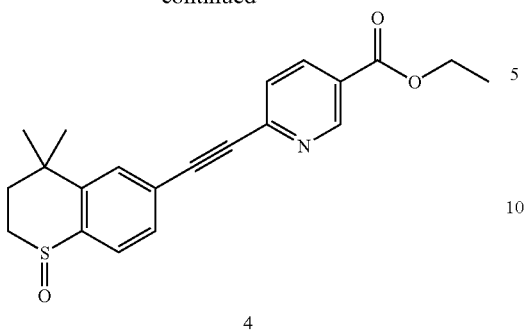

4

In greater detail, 4,4-dimethyl-6-bromothiochromane is easily obtained according to known techniques, from commercial products such as 4-bromothiophenol and 3,3-dimethylallyl bromide, then is transformed into the corresponding S-oxide (5) by controlled oxidation according to conventional procedures, preferably with a peroxy acid, such as peracetic, performic or 3-chloroperbenzoic acid. The reaction is carried out in stoichiometric ratios, at low temperatures and in diluted solutions thereby avoiding formation of the sulfone; chloroalkanes such as dichloromethane or chloroform are used as the solvents, at temperatures around 0° C. Compound (5) is converted to (7) by reaction with 2-methyl-3-butyn-2-ol (6) in the presence of palladium on carbon, copper(I) iodide, triphenylphosphine, potassium carbonate in dimethoxyethane/water at about 80° C. (Bleicher, L. S.; Cosford, N. D. P.; Herbaut A.; McCallum; J. S.; McDonald, I. A. J. Org. Chem. 1998, 63, 1109-1118), in yields above 80%. Adduct (7) is converted to 4,4-dimethyl-6-ethynylthiochromane-S-oxide (8) according to one of the conventional processes for deprotecting this type of acetylenes under basic hydrolysis conditions. The preferred treatment to obtain (8) from (7) is refluxing in toluene with sodium hydride in catalytic amounts (Havens, S. J.; Hergenrother, P. M. J. Org. Chem. 1985, 50. 1763-1765).

Conversion of (8) to (2) is carried out directly by adding a solution of (8) in N,N-dimethylformamide, at about −20° C., with $PCl_3$ in stoichiometric amount (Madesclaire, M. Tetrahedron 1988, 44, 6537-6580). The reaction mixture is then diluted in ice and extracted with a suitable solvent to yield compound (2). In case (8) is converted to (4), condensation with ethyl 6-chloronicotinate (3) is carried out in the presence of bis(triphenylphosphine) palladium(II) dichloride, copper(I) iodide, triethylamine in N,N-dimethylformamide, heating to 50° C.: Tazarotene-S-oxide (4) is recovered in 80-85% yields as a crystalline solid (crystallization is carried out in, e.g., hexane/ethyl acetate). Finally, deoxygenation of (4) to (1) is carried out analogously to what described above for the preparation of (2) from (8). In this instance, Tazarotene (1) is recovered in 60-70% yields and purified by crystallization from hexane.

Ethyl 6-ethynylpiridin-3-carboxylate (10) used in the alternative synthesis of (4) is obtained from (3) by condensation with butynol (6) under conditions similar to those for the preparation of (9) and hydrolysis of the latter to (10). Condensation of (10) with 4,4-dimethyl-6-bromothiochromane-S-oxide (6) affords (4), thus representing an alternative synthesis for (1).

The following examples further illustrate the process of the invention. The structure of the various compounds was confirmed by elemental analysis and $^1H$ NMR spectra recorded in $CDCl_3$ solution at room temperature with a spectrometer Bruker AC-400 (400 MHz $^1H$), unless otherwise indicated. Chemical shifts are based on tetramethylsilane as an internal standard.

EXAMPLE 1

Preparation of 4,4-dimethyl-6-bromothiochromane-6-oxide (5)

a) 4-Bromothiophenol (12.0 g, 63.5 mmols) dissolved in acetone (75 ml) is added with finely ground solid sodium hydroxide (2.54 g, 63.5 mmols) under stirring. When sodium hydroxide is completely dissolved, 3,3-dimethylallyl bromide (9.46 g, 63.5 mmols) dissolved in acetone (20 ml) is added dropwise. After completion of the addition, the mixture is refluxed for 1 hour 30 min, then the reaction crude is cooled and the solvent is evaporated off. The residue is taken up with 50 ml of water and extracted with ether (3×50 ml). The organic phase is washed with water and a sodium chloride saturated solution. The organic phase is dried over sodium sulfate, filtered and concentrated evaporated in vacuo, thereby obtaining 19.2 g of a crude which is purified by column chromatography (eluent: hexane/ethyl acetate=9:1).

b) The resulting product is dropped into a suspension of $P_2O_5$ (9.0 g, 63.5 mmols) in methanesulfonic acid (54 ml). The reaction mixture is vigorously stirred for 2 hours at room temperature, then poured in ice and extracted with ether (3×100 ml). The combined organic phases are washed with a sodium chloride saturated solution, dried over sodium sulfate, filtered and concentrated evaporated in vacuo. The resulting reaction crude is crystallized from hexane (70 ml).

c) The separated solid (15.1 g, 58.5 mmols) is dissolved in methylene chloride (300 ml) and the resulting solution is cooled to 0° C.; 75% 3-chloroperbenzoic acid (13.8 g, 79.9 mmol) is added in small portions. After completion of the addition, the reaction mixture is stirred for 1 hour, then brought to room temperature keeping stirring for a further 2 hours. The reaction crude is then diluted with methylene chloride (150 ml), washed with a sodium pyrosulfite solution and a sodium hydrogencarbonate diluted solution. The organic phase is dried over sodium sulfate, filtered and concentrated evaporated in vacuo, thereby obtaining a solid which is crystallized from hexane (60 ml) and ethyl acetate (40 ml) to give the desired compound (5) (12.5 g, yield=72%; m.p.=120-122° C.). $^1H$ NMR δ 1.31(3H, s), 1.45 (3H, s), 1.87 (1H, ddd, J=2.6, 8.4, 15.0 Hz), 2.45 (1H, ddd, J=2.6, 10.5, 15.0 Hz), 3.12 (2H, m), 7.49 (1H, dd, J=1.9, 8.3 Hz), 7.58 (1H, d, J=1.9 Hz), 7.61 (1H, d, J=8.3 Hz).

EXAMPLE 2

Preparation of 4-[(4,4-dimethyl)-thiochroman-6-yl]-2-methyl-3-butyn-2-ol-S-oxide (7)

Intermediate (5) (7.94 g, 29.0 mmol) is dissolved in dimethoxyethane (120 ml) and added in succession with water (55 ml), potassium carbonate (10.01 g, 72.45 mmol), copper(I) iodide (0.22 g, 1.16 mmol), triphenylphosphine (0.60 g, 2.32 mmol) and 10% (w/w) palladium on carbon (0.62 g, 0.58 mmol). The reaction mixture is stirred for 30 minutes at room temperature, then added with 2-methyl-3-butyn-2-ol (7.1 ml, 72.45 mmol) and heated at 80° C. for 5 hours. The reaction mixture is then cooled, filtered through Celite, diluted with water (400 ml) and extracted with ethyl acetate (2×300 ml). The organic phase is washed with water, dried over sodium sulfate, filtered and concentrated evaporated in vacuo. The resulting reaction crude is purified by column chromatography (eluent:hexane: ethyl acetate=2:1) and crystallized from hexane (15 ml) and ethyl acetate (45 ml) thereby obtaining 6.61 g of compound (7) (yield=83%; m.p.=109-110° C.). $^1$H NMR δ 1.31 (3H, s), 1.45 (3H, s), 1.63 (6H, s), 1.87 (1H, ddd, J=2.3, 8.6, 14.7 Hz), 2.45 (1H, ddd, J=2.3, 10.5, 14.7 Hz), 3.12 (2H, m), 7.37 (1H, dd, J=1.6, 8.1 Hz), 7.47 (1H, d, J=1.6 Hz), 7.68 (1H, d, J=8.1 Hz).

EXAMPLE 3

Preparation of 4,4-dimethyl-6-ethynylthiochromane-S-oxide (8) from (7)

Compound (7) (32.86 g, 119.1 mmol) is dissolved in toluene (400 ml) and added with 60% sodium hydride (400 mg, 16.7 mmol) in small portions under stirring. The reaction mixture is heated to 110° C. for 1 hour, while distilling off the toluene/acetone mixture with a Claisen adapter (200 ml). The mixture is left to cool, concentrated evaporated in vacuo, taken up with ether (400 ml) and washed with a 1M potassium carbonate solution, water and a sodium chloride saturated solution. The organic phase is dried, filtered and concentrated evaporated in vacuo thereby obtaining 21.7 g of the desired product (yield=84%; m.p.=105-107° C.). $^1$H NMR δ 1.32(3H, s), 1.45 (3H, s), 1.88 (1H, ddd, J=2.5, 8.8, 15.1 Hz), 2.44 (1H, ddd, J=2.5, 10.3, 15.1 Hz), 3.08 (1H, ddd, J=2.5, 8.8, 13.1 Hz), 3.17 (1H, s), 3.19 (1H, m), 7.46 (1H, dd, J=1.5, 8.1 Hz), 7.56 (1H, d, J=1.5 Hz), 7.71 (1H, d, J=8.1 Hz).

EXAMPLE 4

Preparation of 4,4-dimethyl-6-ethynylthiochromane (2) from (8)

Compound (8) (10.0 g, 45.87 mmol) is dissolved in N,N-dimethylformamide (150 ml), cooled to −20° C., added with phosphorous trichloride (4.0 ml, 45.87 mmol) and stirred for 1 hr, then the reaction crude is diluted with ethyl acetate (200 ml), washed with a sodium chloride saturated solution and with water. The organic phase is dried over sodium sulfate, filtered and concentrated evaporated in vacuo. The resulting solid is subjected to column chromatography (eluent:hexane/ethyl acetate=9:1) thereby obtaining 7.88 g of the desired product (yield=85%; oil). $^1$H NMR (250 MHz) δ 1.35 (6H, s), 1.95 (2H, m), 3.05 (2H, m), 3.15 (1H, s), 7.13 (1H, d, J=8.6 Hz), 7.58 (1H, dd, J=8.6, 2.0 Hz), 7.99 (1H, d, J=2.0 Hz).

EXAMPLE 5

Preparation of ethyl 6-[2-(4,4-dimethylthiochroman-6-yl)ethynyl]nicotinate S-oxide (4) from (8) and (3)

Compound (3) (21.24 g, 114.5 mmols), triethylamine (60 ml) and (8) (21.7 g, 99.54 mmol) are dissolved in N,N-dimethylformamide (400 ml) and added with copper(I) iodide (2.37 g, 12.44 mmol) and bis(triphenylphosphine) palladium (II) dichloride (5.93 g, 8.46 mmol), under nitrogen. The reaction mixture is heated at 50° C. under stirring for 3 hours, then left to cool and the reaction crude is diluted with ethyl acetate (600 ml) and washed with water. The aqueous phases are re-extracted with ethyl acetate (2×200 ml). The combined organic phases are washed with water, dried over sodium sulfate, filtered and concentrated evaporated in vacuo. The resulting reaction crude is subjected to column chromatography (eluent:hexane:ethyl acetate=5:2), then crystallized from hexane (90 ml) and ethyl acetate (10 ml) thereby obtaining 29.0 g of the desired product (yield=79%; m.p.=144-146° C.). $^1$H NMR δ 1.34 (3H, s), 1.43 (3H, t, J=7.1 Hz), 1.48 (3H, s), 1.91 (1H, ddd, J=2.4, 8.9, 15.1 Hz), 2.45 (1H, ddd, J=2.4, 10.1, 15.1 Hz), 3.16 (2H, m), 4.45 (2H, q, J=7.1 Hz), 7.58 (1H, dd, J=1.6, 8.1 Hz), 7.62 (1H, m), 7.71 (1H, d, J=1.6 Hz), 7.78 (1H, d, J=8.1 Hz), 8.31 (1H, dd, J=2.1, 8.1 Hz), 9.23 (1H, m).

EXAMPLE 6

Preparation of Tazarotene from ethyl 4,4-dimethylthiochroman-6-yl)ethynyl]nicotinate S-oxide (4)

Compound (4) (29.0 g, 79.0 mmol) is dissolved in N,N-dimethylformamide (500 ml), cooled to −20° C., added with phosphorous trichloride (6.9 ml, 79.0 mmol) and stirred for 1 hr, then the reaction crude is diluted with ethyl acetate (400 ml), washed with a sodium chloride saturated solution and water. The organic phase is dried over sodium sulfate, filtered and concentrated evaporated in vacuo. The resulting solid is subjected to column chromatography (eluent:hexane:ethyl acetate=9:1) and crystallized from hexane (100 ml) thereby obtaining 16.4 g of the desired product (yield=59%; m.p.=97-98° C.). $^1$H NMR δ 1.34 (6H, s), 1.42 (3H, t, J=7.1 Hz), 1.96 (2H, m), 3.05 (2H, m), 4.42 (2H, q, J=7.1 Hz), 7.08 (1H, d, J=8.0 Hz), 7.25 (1H, dd, J=1.8, 8.0 Hz), 7.55 (1H, d, J=8.0 Hz), 7.62 (1H, d, J=1.8 Hz), 8.26 (1H, dd, J=2.1, 8.0 Hz), 9.23 (1H, d, J=2.1 Hz).

EXAMPLE 7

Preparation of ethyl 6-[(3-methyl-3-hydroxy)butyn-1-yl]nicotinate (9) from ethyl 6-chloronicotinate (3)

Compound (3) (7.0 g, 37.72 mmol) is dissolved in dimethoxyethane (200 ml) and added in succession with water (90 ml), potassium carbonate (20.85 g, 150.88 mmol), copper(I) iodide (0.29 g, 1.5 mmols), triphenylphosphine (0.79 g, 3.01 mmol) and 10% (w/w) palladium on carbon (0.80 g, 0.75 mmol). The reaction mixture is stirred for 30 minutes at room temperature, then added with 2-methyl-3-butyn-2-ol (14.7 ml, 150.88 mmol), heated at 80° C. for 2 hours 30 minutes, then cooled, filtered through Celite, diluted with water (400 ml) and extracted with ethyl acetate (2×300 ml). The organic phase is washed with water, dried over sodium sulfate, filtered and concentrated evaporated in vacuo. The resulting reaction crude is subjected to column chromatography (eluent:hexane:ethyl acetate=9:1) thereby obtaining 6.1 g of compound (9) (yield =69%; oil). $^1$H NMR δ 1.40 (3H, t, J=7.1 Hz), 1.65 (6H, s), 4.40 (2H, q, J=7.1 Hz), 7.50 (1H, dd, J=0.7, 8.0 Hz), 8.20 (1H, dd, J=2.1, 8.0 Hz), 9.10 (1H, dd, J=0.7, 2.1 Hz).

EXAMPLE 8

Preparation of ethyl 6-ethynylnicotinate (10) from (9)

Compound (9) (6.86 g, 29.44 mmol) is dissolved in toluene (200 ml), added with 60% sodium hydride (99 mg, 4.1 mmol) in small portions under stirring, and heated to 110° C. for 1 hr, while distilling off the toluene/acetone mixture with a Claisen adapter (100 ml). The reaction mixture is cooled and concentrated evaporated in vacuo, taken up with ether (150 ml) and washed with a 0.5 M potassium carbonate solution. The aqueous phase is extracted with ether (2×70 ml), the combined organic phases are washed with a sodium chloride saturated solution, dried, filtered and concentrated evaporated in vacuo. The resulting reaction crude is subjected to column chromatography (eluent:hexane/ethyl acetate=95:5) thereby obtaining 3.73 g of the desired product (yield=72%; m.p.=49-51° C.). $^1$H NMR δ 1.41 (3H, t, J=7.1 Hz), 3.30 (1H, s) 4.42 (2H, q, J=7.1 Hz), 7.54 (1H, d, J=8.1 Hz), 8.26 (1H, dd, J=2.1, 8.1 Hz), 9.17 (1H, d, J=2.1 Hz).

EXAMPLE 9

Preparation of ethyl 6-[2-(4,4-dimethylthiochroman-6-yl)ethynyl]nicotinate S-oxide (4) from (5) and (10)

Compound (5) (5.4 g, 19.71 mmol), triethylamine (45 ml) and (10) (3.0 g, 17.14 mmol) are dissolved in N,N-dimethylformamide (45 ml), then added with copper(I) iodide (0.41 g, 2.14 mmol) and bis(triphenylphosphine) palladium (II) dichloride (0.90 g, 1.29 mmol). The reaction mixture is heated to 50° C. under stirring for 3 hours, then cooled and the reaction crude is diluted with ethyl acetate (200 ml) and washed with water. The aqueous phases are re-extracted with ethyl acetate (2×70 ml). The combined organic phases are washed with water, dried over sodium sulfate, filtered and concentrated evaporated in vacuo. The resulting reaction crude is subjected to column chromatography (eluent: hexane:ethyl acetate=9:1), then crystallized from hexane (27 ml) and ethyl acetate (3 ml) thereby obtaining 3.6 g of the desired product (yield=57%; m.p.=144-146° C.). $^1$H NMR δ 1.34 (3H, s), 1.43 (3H, t, J=7.1 Hz), 1.48 (3H, s), 1.91 (1H, ddd, J=2.4, 8.9, 15.1 Hz), 2.45 (1H, ddd, J=2.4, 10.1, 15.1 Hz), 3.16 (2H, m), 4.45 (2H, q, J=7.1 Hz), 7.58 (1H, dd, J=1.6, 8.1 Hz), 7.62 (1H, m), 7.71 (1H, d, J=1.6 Hz), 7.78 (1H, d, J=8.1 Hz), 8.31 (1H, dd, J=2.1, 8.1 Hz), 9.23 (1H, m).

The invention claimed is:

1. A process for the preparation of ethyl 6-[2-(4,4-dimethylthiochroman-6-yl)ethynyl]nicotinate (Tazarotene) of formula (1), comprising deoxygenating the corresponding ethyl 6-[2-(4,4-dimethylthiochroman-6-yl)ethynyl]nicotinate S-oxide of formula (4) according to the scheme below:

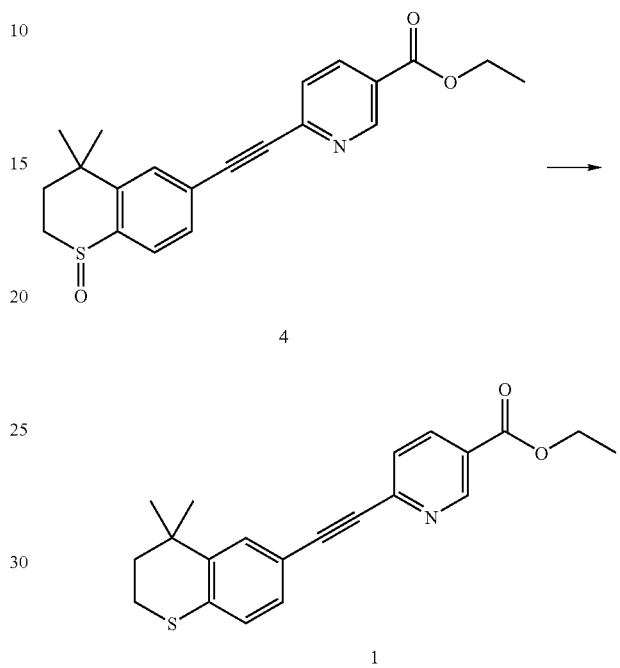

wherein the deoxygenation of (4) to (1) is carried out with phosphorous trichloride in dimethylformamide.

2. The process as claimed in claim 1, which is carried out at temperatures ranging from −25° C. to −15° C.